(12) United States Patent
Annis

(10) Patent No.: US 8,013,155 B2
(45) Date of Patent: Sep. 6, 2011

(54) METHOD FOR PREPARING SUBSTITUTED PYRIMIDINES

(75) Inventor: Gary David Annis, Landenberg, PA (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 831 days.

(21) Appl. No.: 11/886,653

(22) PCT Filed: May 12, 2006

(86) PCT No.: PCT/US2006/018522
§ 371 (c)(1),
(2), (4) Date: Sep. 17, 2007

(87) PCT Pub. No.: WO2006/124657
PCT Pub. Date: Nov. 23, 2006

(65) Prior Publication Data
US 2009/0054647 A1 Feb. 26, 2009

Related U.S. Application Data

(60) Provisional application No. 60/681,298, filed on May 16, 2005.

(51) Int. Cl.
C07D 239/46 (2006.01)
C07D 239/48 (2006.01)
(52) U.S. Cl. .................. 544/319; 544/326; 544/334
(58) Field of Classification Search .................. 544/319, 544/326, 334
See application file for complete search history.

(56) References Cited

U.S. PATENT DOCUMENTS

| | | | |
|---|---|---|---|
| 6,200,977 B1 | 3/2001 | Cushing et al. | |
| 6,528,513 B2 | 3/2003 | Cushing et al. | |
| 6,835,726 B2 | 12/2004 | Cushing et al. | |
| 2003/0130264 A1 | 7/2003 | Jaen | |
| 2005/0059687 A1 | 3/2005 | Makings et al. | |
| 2007/0197391 A1* | 8/2007 | Clark et al. | 504/236 |
| 2009/0043098 A1 | 2/2009 | Shapiro | |

FOREIGN PATENT DOCUMENTS

| | | |
|---|---|---|
| CA | 207185 A | 4/1991 |
| EP | 1200414 A1 | 5/2002 |
| EP | 1646615 A1 | 4/2006 |
| GB | 2095240 | 9/1982 |
| WO | 91/06541 A | 5/1991 |
| WO | 99/41253 A | 8/1999 |
| WO | 02/064096 A3 | 8/2002 |
| WO | 2005063721 A1 | 7/2005 |

OTHER PUBLICATIONS

Nishihara et al., J. Org. Chem., 25(6), 2525-2526, 1968.*
Karimi et al., Efficient Aerobic Oxidation of Acetals to Esters Catalysed by N-Hydroxyphtalimide and Co(II) Under Mild Conditions, 2003, vol. 15:2373-2377.
Chidambaram et al., A Highly Selective Methodology for the Direct Conversion of Acetals to Esters, J. Org. Chem., 1992, vol. 57:5013-5015.

* cited by examiner

Primary Examiner — Venkataraman Balasubramanian

(57) ABSTRACT

Disclosed a method for preparing a compound of Formula 1,

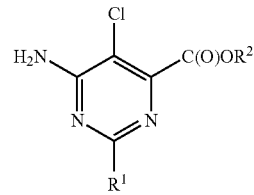

1 wherein $R^1$ is cyclopropyl, 4-chlorophenyl or 4-bromophenyl; and $R^2$ is $C_1$-$C_{14}$ alkyl; comprising contacting a compound of Formula 2

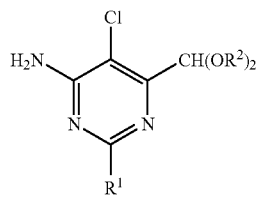

2 with a persulfate oxidant in the presence of a strong sulfur- or phosphorus-containing mineral acid and an oxidation resistant solvent. Also disclosed are methods for preparing the compound of Formula 2 from a compound of Formula 5

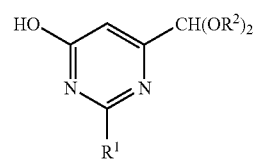

5 as well as compounds of Formula 6 and salts thereof,

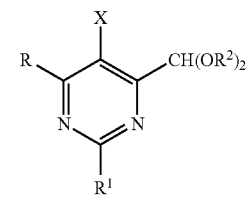

6 wherein R is $NH_2$, Cl or OH; X is H or Cl; $R^1$ is cyclopropyl, 4-chlorophenyl or 4-bromophenyl; and $R^2$ is $C_1$-$C_{14}$ alkyl; provided that when R is $NH_2$ or Cl, then X is Cl; which are useful a process intermediates.

16 Claims, No Drawings

METHOD FOR PREPARING SUBSTITUTED PYRIMIDINES

This application is a 371 of PCT/US2006/018522, filed May 12, 2006, which claims benefit of U.S. Provisional Application No. 60/681,298, filed May 16, 2005.

FIELD OF THE INVENTION

This invention relates to a method for preparing 2-substituted 6-amino-5-chloro-4-pyrimidinecarboxylate esters and to pyrimidines useful as process intermediates in the method.

BACKGROUND OF THE INVENTION

New synthetic methods are desirable to provide compounds of interest as agricultural active ingredients, pharmaceuticals and other fine chemicals in higher yields and purities and at lower costs. Such a method has now been discovered for preparation of 2-substituted 6-amino-5-chloro-4-pyrimidinecarboxylate esters, which are disclosed in PCT Publication WO2005/063721 to be useful as herbicides.

SUMMARY OF THE INVENTION

The present invention relates to a method for preparing a compound of Formula 1,

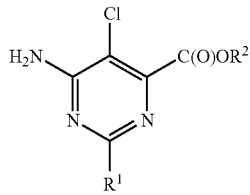

wherein $R^1$ is cyclopropyl, 4-chlorophenyl or 4-bromophenyl; and $R^2$ is $C_1$-$C_{14}$ alkyl; comprising contacting a compound of Formula 2

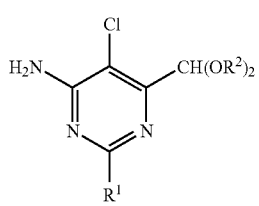

with a persulfate oxidant in the presence of a strong sulfur- or phosphorus-containing mineral acid.

Another aspect of the present invention relates to the aforesaid method further comprising preparing the compound of Formula 2 by contacting a compound of Formula 3

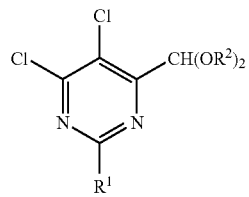

with ammonia.

Another aspect of the present invention relates to the aforesaid method further comprising preparing the compound of Formula 3 by contacting a compound of Formula 4

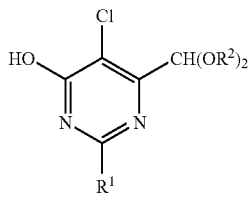

with a dehydroxylating-chlorinating agent selected from phosphorus oxychloride and thionyl chloride in the presence of N,N-dimethylformamide.

Another aspect of the present invention relates to the aforesaid method further comprising preparing the compound of Formula 4 by contacting a compound of Formula 5

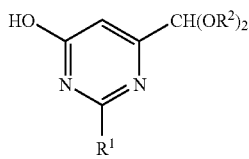

with a chlorinating agent.

Further aspects of the present invention relate to compounds of Formula 6 or salts thereof,

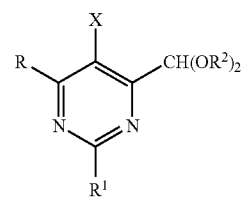

wherein R is $NH_2$, Cl or OH; X is H or Cl; $R^1$ is cyclopropyl, 4-chlorophenyl or 4-bromophenyl; and $R^2$ is $C_1$-$C_{14}$ alkyl; provided that when R is $NH_2$ or Cl, then X is Cl; which are useful as process intermediates in the aforedescribed method.

DETAILED DESCRIPTION OF THE INVENTION

As used herein, the terms "comprises," "comprising," "includes," "including," "has," "having" or any other variation thereof, are intended to cover a non-exclusive inclusion. For example, a composition, process, method, article, or apparatus that comprises a list of elements is not necessarily limited to only those elements but may include other elements not expressly listed or inherent to such composition, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, the indefinite articles "a" and "an" preceding an element or component of the invention are intended to be nonrestrictive regarding the number of instances (i.e. occurrences) of the element or component. Therefore "a" or "an" should be read to include one or at least one, and the singular word form of the element or component also includes the plural unless the number is obviously meant to be singular.

As referred to herein, "alkyl" includes straight-chain or branched alkyl, such as, methyl, ethyl, n-propyl, i-propyl, or the different butyl, pentyl or hexyl isomers.

Combining chemicals refers to contacting the chemicals with each other.

Numeric ranges are inclusive of each and every integer value defining the range.

One skilled in the art recognizes that Formula 6 embraces Formulae 3, 4 and 5. That is when R is $NH_2$, and X is Cl, then Formula 6 is equivalent to Formula 3. When R is OH and X is Cl, then Formula 6 is equivalent to Formula 4. When R is OH and X is H, then Formula 6 is equivalent to Formula 5.

One skilled in the art also recognizes that the compounds of Formulae 4 and 5 are in equilibrium with their respective tautomeric counterparts of Formulae 4a and 5a, as shown in Exhibit 1.

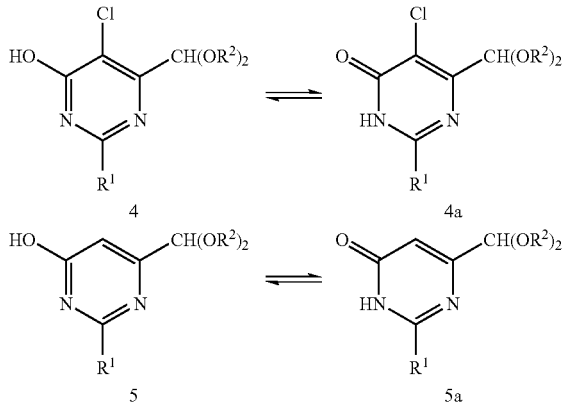

Exhibit 1

Unless expressly stated otherwise, references to Formulae 4 and 5 in the present disclosure and claims are to be construed to include all tautomers, including Formulae 4a and 5a, respectively.

The nitrogen atom in the compounds of Formulae 2, 3 and 4 (including 4a) can be protonated, allowing said compounds to form acid-addition salts with inorganic or organic acids such as hydrobromic, hydrochloric, nitric, phosphoric, sulfuric, acetic, butyric, fumaric, lactic, maleic, malonic, oxalic, propionic, salicylic, tartaric, 4-toluenesulfonic or valeric acids.

Embodiments of the present invention include:

Embodiment A1. A method for preparing a compound of Formula 1 wherein $R^1$ is cyclopropyl.

Embodiment A2. A method for preparing a compound of Formula 1 wherein $R^1$ is 4-chlorophenyl or 4-bromophenyl.

Embodiment A3. A method for preparing a compound of Formula 1 wherein $R^2$ is $C_1$-$C_8$ alkyl.

Embodiment A4. A method of Embodiment A3 wherein $R^2$ is $C_1$-$C_3$ alkyl.

Embodiment A5. A method of Embodiment A4 wherein $R^2$ is methyl.

Embodiment B1. A method for preparing the compound of Formula 1, comprising contacting a compound of Formula 2 with a persulfate oxidant in the presence of a strong sulfur- or phosphorus-containing mineral acid.

Embodiment B2. A method of Embodiment B1 wherein the persulfate oxidant comprises an ammonium or alkali metal cation.

Embodiment B3. A method of Embodiment B2 wherein the persulfate oxidant comprises ammonium persulfate.

Embodiment B4. A method of Embodiment B2 wherein the persulfate oxidant comprises potassium persulfate.

Embodiment B5. A method of Embodiment B2 wherein the persulfate oxidant comprises potassium peroxymonosulfate.

Embodiment B6. A method of Embodiment B2 wherein the persulfate oxidant comprises sodium persulfate.

Embodiment B7. A method of Embodiment B1 wherein the molar ratio of the persulfate in the persulfate oxidant to the compound of Formula 2 is in a range of about 1 to about 3.

Embodiment B8. A method of Embodiment B7 wherein the molar ratio is in a range of about 1.1 to about 2.2.

Embodiment B9. A method of Embodiment B1 wherein the strong sulfur- or phosphorus-containing mineral acid is sulfuric acid or phosphoric acid.

Embodiment B10. A method of Embodiment B9 wherein the strong sulfur- or phosphorus-containing mineral acid is sulfuric acid.

Embodiment B11. A method of Embodiment B1 wherein the molar ratio of the strong sulfur- or phosphorus-containing mineral acid to the compound of Formula 2 is in a range of about 1 to about 3.

Embodiment B12. A method of Embodiment B11 wherein the molar ratio is in a range of about 1.1 to about 2.2.

Embodiment B13. A method of Embodiment B1 wherein the contacting is performed in the presence of an oxidation resistant solvent.

Embodiment B14. A method of Embodiment B13 wherein the oxidation resistant solvent is an alkane nitrile;

Embodiment B15. A method of Embodiment B14 wherein the oxidation resistant solvent is acetonitrile or propionitrile.

Embodiment B16. A method of Embodiment B15 wherein the oxidation resistant solvent is acetonitrile.

Embodiment B17. A method of Embodiment B1 wherein the compound of Formula 2 is contacted with the persulfate oxidant at a temperature in a range of about 0 to about 40° C.

Embodiment B18. A method of Embodiment B17 wherein the temperature is in a range of about 25 to about 35° C.

Embodiment C1. A method of Embodiment B further comprising preparing the compound of Formula 2 by contacting a compound of Formula 3 with ammonia.

Embodiment C2. A method of Embodiment C1 wherein the molar ratio of ammonia to the compound of Formula 3 is at least about 2.

Embodiment C3. A method of Embodiment C2 wherein the molar ratio of ammonia to the compound of Formula 3 is in a range of about 2 to about 20.

Embodiment C4. A method of Embodiment C3 wherein the molar ratio of ammonia to the compound of Formula 3 is in a range of about 5 to about 15.

Embodiment C5. A method of Embodiment C1 wherein the contacting is performed in an non-acidic organic solvent Embodiment C6. A method of Embodiment C5 wherein the non-acidic organic solvent comprises an ether, alcohol or aromatic solvent.

Embodiment C7. A method of Embodiment C6 wherein the non-acidic organic solvent comprises at least one of tetrahydrofuran, p-dioxane, methanol, ethanol, n-propanol, isopropanol, n-butanol, sec-butanol, toluene and xylenes.

Embodiment C8. A method of Embodiment C7 wherein the non-acidic organic solvent comprises ethanol.

Embodiment C9. A method of Embodiment Cl wherein the ammonia is at a pressure above atmospheric pressure.

Embodiment C10. A method of Embodiment C9 wherein the pressure above atmospheric pressure is between about 100 to about 1000 kPa.

Embodiment C11. A method of Embodiment C10 wherein the pressure above atmospheric pressure is between about 200 and about 500 kPa.

Embodiment C12. A method of Embodiment Cl wherein the compound of Formula 3 is contacted with ammonia at a temperature in a range of about 0 to about 40° C. and then the temperature is raised to a range of about 60 to about 100° C.

Embodiment C13. A method of Embodiment C12 wherein the contacting is at a temperature in a range of about 10 to about 30° C. and then the temperature is raised to a range of about 70 to about 80° C.

Embodiment D1. A method of Embodiment C1 further comprising preparing the compound of Formula 3 by contacting a compound of Formula 4 with a dehydroxylating-chlorinating agent selected from phosphorus oxychloride and thionyl chloride in the presence of N,N-dimethylformamide.

Embodiment D2. A method of Embodiment D1 wherein the dehydroxylating-chlorinating agent is phosphorus oxychloride.

Embodiment D3. A method of Embodiment D1 wherein the molar ratio of the dehydroxylating-chlorinating agent to the compound of Formula 4 is in a range of about 1 to about 1.5.

Embodiment D4. A method of Embodiment D3 wherein the molar ratio of the dehydroxylating-chlorinating agent to the compound of Formula 4 is in a range of about 1.1 to about 1.3.

Embodiment D5. A method of Embodiment D1 wherein the contacting is performed in an aprotic solvent.

Embodiment D6. A method of Embodiment D5 wherein the aprotic solvent comprises at least one solvent selected from haloalkanes, haloalkenes, halobenzenes, toluene, xylenes and N,N-dimethylformamide.

Embodiment D7. A method of Embodiment D6 wherein the aprotic solvent comprises at least one solvent selected from dichloromethane, 1,2-dichloroethane, chlorobenzene, toluene and N,N-dimethylformamide.

Embodiment D8. A method of Embodiment D7 wherein the aprotic solvent comprises toluene.

Embodiment D9. A method of Embodiment D1 wherein the compound of Formula 4 is contacted with the dehydroxylating-chlorinating agent at a temperature in a range of about −5 to about 40° C.

Embodiment D10. A method of Embodiment D9 wherein the compound of Formula 4 is contacted with the dehydroxylating-chlorinating agent at about ambient temperature.

Embodiment E1. A method of Embodiment D1 further comprising preparing the compound of Formula 4 by contacting a compound of Formula 5 with a chlorinating agent.

Embodiment E2. A method of Embodiment E1 wherein the chlorinating agent is selected from the group consisting of (a) a combination of elemental chlorine and an alkali metal salt of a carboxylic acid, and (b) sodium hypochlorite.

Embodiment E3. A method of Embodiment E2 wherein the chlorinating agent is a combination of elemental chlorine and an alkali metal salt of a carboxylic acid.

Embodiment E4. A method of Embodiment E3 wherein the wherein the contacting is performed in the presence of a carboxylic acid.

Embodiment E5. A method of Embodiment E4 wherein the chlorinating agent is a combination of elemental chlorine, sodium acetate and acetic acid.

Embodiment E6. A method of Embodiment E2 wherein the chlorinating agent is sodium hypochlorite.

Embodiment E7. A method of Embodiment E6 wherein the contacting is performed in a solvent that comprises a mixture of water and at least one solvent selected from alcohols, carboxylic acids, haloalkanes, haloalkenes, halobenzenes, toluene and xylenes.

Embodiment E8. A method of Embodiment E7 wherein the solvent comprises a mixture of water and toluene, methanol or acetic acid.

Embodiment E9. A method of Embodiment E1 wherein the molar ratio of chlorinating agent to the compound of Formula 5 is in a range of about 0.98 to about 2.

Embodiment E10. A method of Embodiment E3 wherein the molar ratio of elemental chlorine to the compound of Formula 5 is in a range of about 0.98 to about 1.00.

Embodiment E11. A method of Embodiment E3 wherein the molar ratio of the alkali metal salt of the carboxylic acid to the compound of Formula 5 is in a range of about 1 to about 1.2.

Embodiment E12. A method of Embodiment E1 wherein the compound of Formula 5 is contacted with the chlorinating agent at a temperature in a range of about 20 to about 35° C.

Embodiment E13. A method of Embodiment E12 wherein the compound of Formula 5 is contacted with the chlorinating agent at a temperature in a range of about 25 to about 35° C.

Embodiment F1. A compound of Formula 6 or a salt thereof wherein R is $NH_2$, Cl or OH; X is H or Cl; $R^1$ is cyclopropyl, 4-chlorophenyl or 4-bromophenyl; and $R^2$ is $C_1$-$C_{14}$ alkyl, provided that when R is $NH_2$ or Cl, then X is Cl.

Embodiment F2. A compound of Embodiment F1 wherein R is $NH_2$.

Embodiment F3. A compound of Embodiment F1 wherein R is Cl.

Embodiment F4. A compound of Embodiment F1 wherein R is OH.

Embodiment F5. A compound of Embodiment F1 wherein R is $NH_2$, Cl or OH, and X is Cl.

Embodiment F6. A compound of any one of Embodiments F1 to F5 wherein $R^1$ is cyclopropyl.

Embodiment F7. A compound of any one of Embodiments F1 to F5 wherein $R^1$ is 4-chlorophenyl or 4-bromophenyl.

Embodiment F8. A compound of Embodiment F7 wherein $R^1$ is 4-chlorophenyl.

Embodiment F9. A compound of Embodiment F7 wherein $R^1$ is 4-bromophenyl.

Embodiment F10. A compound of any one of Embodiments F1 to F5 wherein $R^2$ is $C_1$-$C_8$ alkyl.

Embodiment F11. A compound of Embodiment F10 wherein $R^2$ is $C_1$-$C_3$ alkyl.

Embodiment F12. A compound of Embodiment F10 wherein $R^2$ is methyl.

In the following Schemes 1-5 the definitions of $R^1$ and $R^2$ in the compounds of Formulae 1 through 9 are as defined above in the Summary of the Invention and description of Embodiments unless otherwise indicated.

As is shown in Scheme 1, a method has now been discovered for preparing ester compounds of Formula 1 from the corresponding acetal compounds of Formula 2 by oxidation with persulfate ion, alternatively identified herein as simply persulfate. Persulfate oxidant refers to an oxidant containing persulfate.

The persulfate (alternatively spelled persulphate) ion is believed to have the chemical structural formula $^\ominus OS(O)_2OOS(O)_2O^\ominus$. As persulfate is an anion, reagents containing persulfate (i.e. persulfate oxidants) are generally salts, typically comprising ammonium or an alkali metal as the cation. Commercially available persulfate oxidants include ammonium persulfate, potassium persulfate, potassium peroxymonosulfate (e.g., OXONE®) and sodium persulfate. Ammonium persulfate works particularly well for the present method. A strong sulfur- or phosphorus-containing mineral acid is used in the present method to promote the oxidation reaction. Strong sulfur- or phosphorus-containing mineral acids refers to acids containing sulfur or phosphorus but not carbon and having a $pK_a$ of less than 3. Examples of strong sulfur- or phosphorus-containing mineral acids include sulfuric acid and phosphoric acid. Sulfuric acid, which is available at low cost, works well for the present method. Both the persulfate and the acid are usually used in a molar ratio of in a range of about 1 (i.e. 1:1) to 3 (i.e. 3:1) relative to the substrate, with a molar ratio in a range of about 1.1 to 2.2 preferred.

In the present method a compound of Formula 2 is contacted with the persulfate oxidant in the presence of a strong sulfur- or phosphorus-containing mineral acid and an oxidation resistant solvent. The term "oxidation resistant solvent" refers to solvents that resist oxidation, particularly by persulfate oxidants. The reaction of the present method works particularly well in alkane nitrile solvents, such as, but not limited to, acetonitrile or propionitrile. Acetonitrile gives excellent results and is preferred for reasons including cost and availability. The reaction can be conducted in a temperature range of about 0 to about 40° C., with the range of about 25 to about 35° C. preferred. Compounds of Formula 2 can be isolated by conventional methods such as dilution with water, extraction or crystallization and the like, all of which are well known to one skilled in the art. This method is illustrated in Example 7 below.

It will also be appreciated that the alkoxy moieties in compounds of Formula 1 may undergo facile exchange (J. March, *Advanced Organic Chemistry*, 3rd Ed, Wiley). This transformation can be used to provide compounds of Formula 1 with different $R^2$ groups if desired. This method is illustrated in Example 8 below.

Compounds of Formula 2 can be prepared by treatment of compounds of Formula 3 with ammonia, as illustrated in Scheme 2.

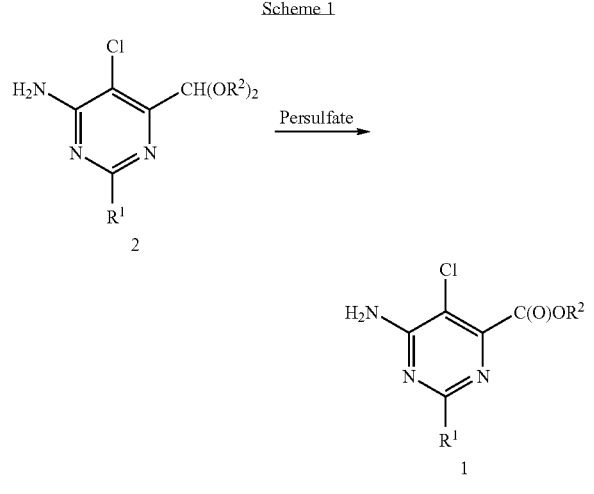

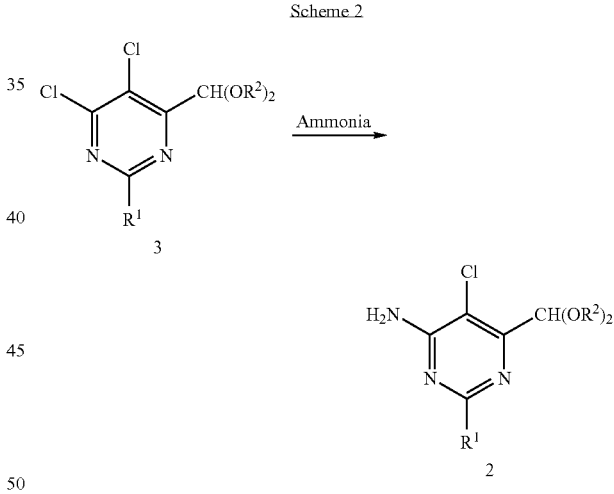

The reaction generates hydrogen chloride as a byproduct, which binds with ammonia to form ammonium chloride salt. Although ammonia can be formed in situ by contact of ammonium salts such as ammonium chloride or ammonium sulfate with bases, the method is most simply and inexpensively conducted by using at least two molar equivalents of ammonia (one molar equivalent to form the compound of Formula 2 and the other molar equivalent to react with the hydrogen chloride formed). Larger amounts of ammonia increase the speed of reaction. The compounds of Formula 3 are thus contacted with ammonia, generally about 2 to about 20 molar equivalents with about 5 to about 15 molar equivalents being preferred, typically in a sealed vessel. This amination method is generally conducted in a solvent (i.e. amination solvent), which can comprise one or more of a wide variety of nonacidic organic solvents, for example, ether, alcohol or aromatic solvents. As particular examples, the amination solvent can comprise tetrahydrofuran, p-dioxane, methanol, ethanol, n-propanol, isopropanol, n-butanol, sec-butanol, toluene or xylenes, with ethanol being preferred. The reaction can be conducted between about 60 and about 100° C. and at a pressure of about 100 to about 1000 kPa to provide an effective concentration of ammonia in the amination solvent. Usually conditions in the preferred temperature range of about 70 to about 80° C. and preferred pressure range of about 200 to about 500 kPa are selected to effect the conversion in approximately 8 h. A preferred procedure involves adding the compound of Formula 3 to the amination solvent containing ammonia at a temperature in a range of about 0 to about 40° C. (preferably about 10 to about 30° C.) and then raising the temperature to a range of about 60 to about 100° C. (preferably about 70 to about 80° C.) to effect the reaction. After removal of the inorganic byproducts the product can be isolated by conventional techniques such as extraction, chromatography or crystallization. This method is illustrated by Example 6 below.

Conversion of the hydroxyl moiety in compounds of Formula 4 to the chloro moiety in compounds of Formula 3 is illustrated in Scheme 3.

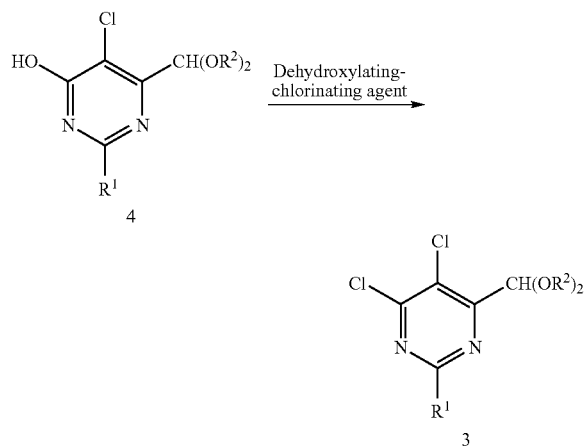

In this method a dehydroxylating-chlorinating agent such as thionyl chloride or more preferably phosphorus oxychloride, is added to a compound of Formula 4 in the presence of N,N-dimethylformamide. A molar ratio of the dehydroxylating-chlorinating agent to the compound of Formula 4 in the range about 1 (i.e. 1:1) to about 1.5 (i.e. 3:2) is operable, with a ratio of about 1.1 to about 1.3 being preferred. The transformation is usually carried out in at least one additional aprotic solvent such as, but not limited to, dichloromethane, 1,2-dichloroethane, chlorobenzene or toluene. Alternatively an excess of N,N-dimethyl-formamide can be used as the solvent. Toluene works very well as a solvent for this method.

The reaction can be conducted in a temperature range of about −5 to about 40° C. After the initial addition of the chlorinating agent at about −5 to about 0° C., the reaction mixture is preferably warmed to about ambient temperature (e.g., about 15-40° C.). After the reaction is complete the reaction mixture is added to aqueous base to consume excess dehydroxylating-chlorinating agent and neutralize acidic byproducts, and the product is isolated by conventional procedures such as distillation, crystallization and the like. This method is illustrated by Example 5 below.

Compounds of Formula 4 can be prepared from compounds of Formula 5 as shown in Scheme 4.

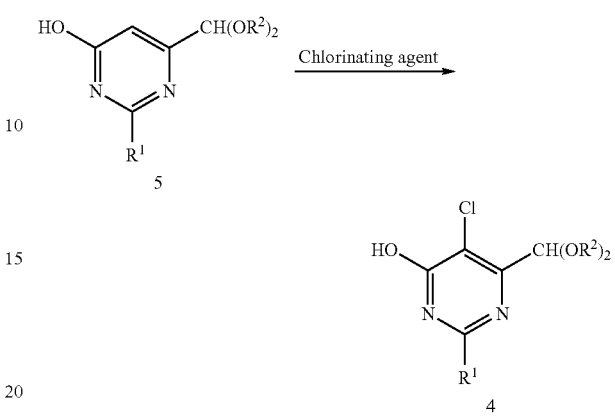

Chlorination can be achieved in a number of ways, such as by chlorination with elemental chlorine or by use of a reagent such as sodium hypochlorite. When chlorine is used, a compatible solvent must be employed, as well as a base to remove hydrogen chloride formed in the reaction. Typically the base used with chlorine is an alkali metal carboxylate. The solvent used with the chlorinating agent comprising chlorine and an alkali metal carboxylate is typically a carboxylic acid, often the carboxylic acid corresponding to the alkali metal carboxylate. For reasons of cost and convenience, sodium acetate is a preferred alkali metal carboxylate and acetic acid is a preferred carboxylic acid for this method. To achieve high yields and purities of the product of Formula 4, the rate of chlorine addition and the temperature of the reaction mixture should be carefully controlled. The total amount of chlorine added should be as close to 1 molar equivalent relative to the compound of Formula 5 as practical. Typically the measured amount of chlorine corresponds to 1.00 molar equivalents, or very slightly less (e.g., 0.98 molar equivalents) to ensure that excess chlorine is not added. The rate of chlorine addition should be such that the temperature of the reaction can be maintained in the range about 20 to about 35° C., preferably in the range of about 25 to about 35° C. The quantity of the base, e.g., alkali metal carboxylate, should be sufficient to absorb the hydrogen chloride generated, and typically is about 1 to about 1.2 molar equivalents. This method is illustrated by Example 4 below.

Alternatively when a reagent such as aqueous sodium hypochloride is used as the chlorinating agent a wide range of chlorination solvents may be employed, such as alcohols, carboxylic acids, haloalkanes, halobenzenes and unhalogenated aromatic hydrocarbons (e.g., toluene, xylenes). Preferred solvents include toluene, methanol and acetic acid. Typically the reaction is conducted at ambient temperature (e.g., about 20-35° C.).

Compounds of Formula 5 can be prepared by combination of a carboximidamide hydrochloride of Formula 7, an ester of a dialkoxy acetate of Formula 8, an ester of acetic acid of Formula 9, and an alkali metal alkoxide base as shown in Scheme 5.

Scheme 5

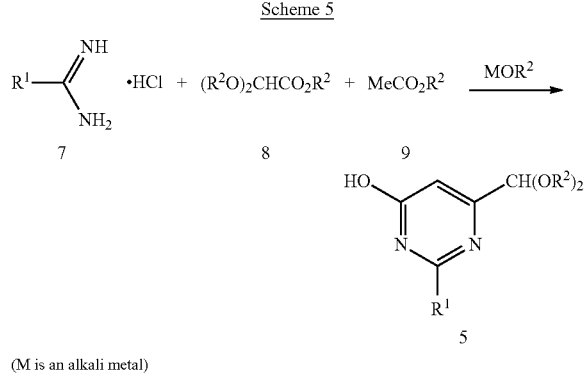

(M is an alkali metal)

Compounds of Formula 8 and Formula 9 are added to an alkali metal alkoxide (i.e. MOR$^2$) such as sodium or potassium methoxide, ethoxide, 1-propoxide, 2-propoxide or t-butoxide in a suitable solvent such as toluene, chlorobenzene or heptane. The alcohol (R$^2$OH) formed is removed by distillation. A sufficient excess of the compound of Formula 9 must be used such that at least one molar equivalent relative to the compound of Formula 8 remains available for the reaction after the alcohol R$^2$OH is removed by distillation, possibly involving azeotropes comprising R$^2$OH, the Formula 9 compound and/or solvent. This step provides the sodium salt of the Claisen condensation product of the compounds of Formula 8 and Formula 9 as an intermediate, which is then condensed with the carboximidamide of Formula 7. Preparation of the Claisen condensation product is illustrated by Example 2 below.

In a typical example where toluene is used as solvent and R$^2$ is Et, the alcohol R$^2$OH is removed by distillation as the ethyl acetate-ethanol azeotrope. When all the alcohol formed by contact of the alkali metal alkoxide with the compounds of Formulae 8 and 9 has been removed, a mixture of the carboximidamide hydrochloride of Formula 7 in ethanol is added at ambient temperature. The reaction mixture can then be boiled to drive the reaction to completion and to remove ethanol as the toluene-ethanol azeotrope, leaving the product in a toluene mixture, from which it can be easily obtained by washing of the toluene solution and evaporation. This method is illustrated by Example 3 below.

Methods for the preparation of amidines of Formula 7 and their salts are well known in the art; see, for example, *J. Chem. Soc.* 1950, 1603 and Japanese patent publication JP 2004/359609. A method of preparation is illustrated by Example 1 below.

Without further elaboration, it is believed that one skilled in the art using the preceding description can utilize the present invention to its fullest extent. The following Examples are, therefore, to be construed as merely illustrative, and not limiting of the disclosure in any way whatsoever. Steps in the following Examples illustrate a procedure for each step in an overall synthetic transformation, and the starting material for each step may not have necessarily been prepared by a particular preparative run whose procedure is described in other Examples or Steps. Percentages are by weight except for chromatographic solvent mixtures or where otherwise indicated. Parts and percentages for chromatographic solvent mixtures are by volume unless otherwise indicated. $^1$H NMR spectra are reported in ppm downfield from tetramethylsilane; "s" means singlet, "d" means doublet, "t" means triplet, "q" means quartet, "m" means multiplet.

Example 1

Preparation of cyclopropanecarboximidamide monohydrochloride in ethanol solution Ethyl cyclopropanecarboximidate monohydrochloride (40.5 g 0.27 mol) was added portionwise to a saturated solution of ammonia in ethanol (50 mL). A further portion of ethanol (33 mL) was added. The mixture was stirred overnight at room temperature. The solvent was removed under reduced pressure, and the residue was dissolved in ethanol to give the title composition (83 mL).

Example 2

Preparation of the sodium salt of ethyl 4,4-diethoxy-3-oxobutanoate in toluene solution Sodium ethoxide in ethanol (21%, 89.5 g, 0.276 mol) was added to toluene (470 mL). The mixture was boiled using a ten-plate Oldershaw column to remove distillate as a ethanol-toluene azeotrope. After a total of about 140 mL of distillate had been removed and the head temperature of the column had risen to 110° C. the mixture was cooled to 80° C. A mixture of ethyl diethoxyacetate (46.3 g, 0.263 mol) and ethyl acetate (101.5 g, 1.15 mol) was added. The mixture was boiled to remove the excess ethyl acetate as an ethyl acetate-ethanol azeotrope.

When the pot temperature reached about 115° C. and the column head temperature reached about 105° C., about 112 mL of distillate had been removed, leaving about 420 mL of residue in the pot. The mixture was then allowed to cool to provide the title composition.

Example 3

Preparation of 2-cyclopropyl-6-(diethoxymethyl)-4 (1H)-pyrimidinone

A portion (~40.4 mL) of the ethanol solution of cyclopropanecarboximidamide monohydrochloride as prepared in Example 1 was added to a portion (~210 mL) of the solution of the sodium salt of ethyl 4,4-diethoxy-3-oxobutanoate as prepared in Example 2. The mixture was allowed to stir overnight at room temperature. The mixture was boiled for about 2 h and then allowed to cool to room temperature. The mixture was evaporated under reduced pressure, and the residue was redissolved in toluene (200 mL). A solution of ammonium chloride (0.68 g, 12.7 mmol) in water (30 mL) was added. After stirring for 10 minutes, the aqueous phase was removed. The organic phase was dried and evaporated to leave the product as pale yellow solid (27.27 g, 88% yield). Product recrystallized from hexanes melted at 111.5-112.0° C.

IR (nujol) 1674, 1602, 1400, 1316, 1153, 1116, 1099, 1068, 1003, 965, 860 cm$^{-1}$.

$^1$H NMR (CDCl$_3$) δ 6.54 (d, J=0.4 Hz, 1H), 5.10 (d, J=0.4 Hz, 1H), 3.70-3.57 (m, 4H), 1.98-1.92 (m, 1H), 1.27-1.05 (m, 10H).

MS m/e (M$^+$+1) calcd. 239.1396, obsd. 239.1395.

Example 4

Preparation of 5-chloro-2-cyclopropyl-6-(diethoxymethyl)-4(1H)-pyrimidinone

Chlorine was carefully passed through 2-cyclopropyl-6-(diethoxymethyl)-4(1H)-pyrimidinone (i.e. the product of Example 3) (46.0 g, 0.193 mol) and sodium acetate (18.8 g, 0.229 mol) in acetic acid (185 mL). The temperature was maintained in the range of about 28-30° C. When the starting material had been consumed, the flow of chlorine was stopped immediately. Toluene (185 mL) was added, and the mixture was evaporated under reduced pressure. The process was repeated. The mixture was partitioned between ethyl acetate (450 mL) and water (50 mL). The organic layer was further washed with water (4×50 mL), dried and evaporated to leave the product as an off-white solid (51.75 g, 98% yield). Product recrystallized from hexanes had a melting point of 109-111° C.

IR (nujol) 1663, 1594, 1402, 1318, 1256, 1145, 1125, 1111, 1100, 1081, 1054, 1039, 1017 $cm^{-1}$.

$^1$H NMR (CDCl$_3$) δ 5.61 (s, 1H), 3.87-3.77 (m, 2H), 3.67-3.57 (m, 2H), 1.99-1.95 (m, 2H), 1.33-1.11 (m, 10H).

MS m/e (M$^+$+1) calcd. 273.1006, obsd. 273.1013.

Example 5

Preparation of 4,5-dichloro-2-cyclopropyl-6-(diethoxymethyl)pyrimidine

Phosphorus oxychloride (35.1 g, 0.229 mol) in toluene (93 mL) was added to 5-chloro-2-cyclopropyl-6-(diethoxymethyl)-4(1H)-pyrimidinone (i.e. the product of Example 4) (51.75 g, 0.190 mol) and N,N-dimethylformamide (34.7 g, 0.475 mol) in toluene (186 mL) at −5 to 0° C. The mixture was allowed to warm to room temperature over about 2 h. Then the mixture was added to aqueous sodium carbonate solution (saturated, 600 mL). The aqueous phase was further extracted with ethyl acetate (4×50 mL), and the organic extracts were combined, dried and evaporated to leave the product as an oil (52.9 g, 95% yield).

IR (film) 1550, 1518, 1429, 1344, 1325, 1310, 1299, 1275, 1251, 1167, 1131, 1069, 1026, 966, 956, 917, 887, 848, 817 $cm^{-1}$.

$^1$H NMR (CDCl$_3$) δ 5.65 (s, 1H), 3.86-3.78 (m, 2H), 3.71-3.60 (m, 2H), 2.30-2.25 (m, 1H), 1.29-1.08 (m, 10H).

MS m/e (M$^+$+1) calcd. 291.0677, obsd. 291.0667.

Example 6

Preparation of 5-chloro-2-cyclopropyl-6-(diethoxymethyl)-4-pyrimidinamine

Ethanol (190 mL) was saturated with ammonia. 4,5-Dichloro-2-cyclopropyl-6-(diethoxymethyl)pyrimidine (i.e. the product of Example 5) (25.2 g, 86.5 mmol) was added, and the mixture sealed in a pressure vessel (Parr Instrument Co., Moline, Ill.). The mixture was warmed to 75° C., and the pressure was maintained at 40 psi (276 kPa). After 8 h at this temperature and pressure the mixture was allowed to cool to room temperature. The solvent was removed under reduced pressure. The residue was dissolved in ethyl acetate (200 mL) and then filtered. The filtrate was evaporated under reduced pressure, and the residue was taken up in hexanes to crystallize the product as an off-white solid (19.97 g, 85% yield). The product recrystallized from hexanes had a melting point of 104.5-109.5° C.

IR (nujol) 3400, 3303, 3174, 3091, 3069, 1678, 1566, 1539, 1398, 1312, 1155, 1123, 1110, 1091, 1056, 1041, 1002 $cm^{-1}$.

$^1$H NMR (CDCl$_3$) δ 5.57 (s, 1H), 5.29 (s, 2H), 3.83-3.75 (m, 2H), 3.69-3.59 (m, 2H), 2.11-2.06 (m, 1H), 1.26 (6H, t), 1.03-0.91 (m, 4H).

MS m/e (M$^+$+1) calcd. 272.1161, obsd. 272.1166.

Example 7

Preparation of ethyl 6-amino-5-chloro-2-cyclopropyl-4-pyrimidinecarboxylate

Sulfuric acid (1.97 g, 20 mmol) was added dropwise to 5-chloro-2-cyclopropyl-6-(diethoxymethyl)-4-pyrimidinamine (i.e. the product of Example 6) (2.71 g, 10 mmol) in acetonitrile (27.5 mL) at room temperature. The temperature rose to 35° C. When the mixture had cooled to 29° C. ammonium persulfate (0.5 g, 2.21 mmol) was added in one portion. After stirring for 20 h at room temperature the mixture was poured into saturated aqueous sodium bicarbonate solution (100 mL). The mixture was extracted with ethyl acetate (2×70 mL). The combined extracts were dried and evaporated to leave the product as an off-white solid (1.32 g, 55% yield). Product purified by chromatography on silica gel (eluted with 40:60 ethyl acetate-hexanes) followed by washing with hydrochloric acid (1 N) melted at 93-95° C.

IR (nujol) 3428, 3389, 3317, 3155, 1727, 1644, 1560, 1534, 1448, 1431, 1406, 1316, 1237, 1089, 1026, 933 $cm^{-1}$.

$^1$H NMR (CDCl$_3$) δ 5.41 (s, 1H), 4.44 (q, 2H), 2.11-2.02 (m, 1H), 1.41 (t, 3H), 1.07-0.94 (m, 4H).

MS m/e (M$^+$+1) calcd. 242.0696, obsd. 242.0689.

Example 8

Preparation of methyl 6-amino-5-chloro-2-cyclopropyl-4-pyrimidinecarboxylate

Sodium methoxide in methanol (25%, 3 drops) was added to ethyl 6-amino-5-chloro-2-cyclopropyl-4-pyrimidinecarboxylate (i.e. the product of Example 7) (0.53 g) in methanol (15 mL). The mixture was boiled for 1 h. The mixture was allowed to cool to room temperature, and was partitioned between hydrochloric acid (0.28 g, 1.16 mmol) in methanol (5 mL). The mixture was boiled for 90 minutes. The mixture was allowed to cool to room temperature, and ammonium chloride (0.3 g, 5.6 mmol) was added. After 10 minutes the solvent was removed under reduced pressure. The mixture was extracted with ethyl acetate (50 mL), and the extracts evaporated to give the product as a white solid (0.24 g, 92% yield). Product recrystallized from ethyl acetate melted at 148.5-149.5° C.

IR (nujol) 3414, 3321, 3138, 1730, 1649, 1563, 1534, 1491, 1437, 1390, 1318, 1243, 1090, 1027, 977, 910, 823, 802 $cm^{-1}$.

$^1$HNMR (CDCl$_3$) δ 5.42 (s, 2H), 3.97 (s, 3H), 2.11-2.02 (m, 1H), 1.08-0.94 (m, 4H).

By the present method, the following compounds of Tables 1-4 can be prepared. The following abbreviations are used in the Tables which follow: i means iso, Pr means propyl, i-Pr means isopropyl, c-Pr means cyclopropyl, Bu means butyl and i-Bu means isobutyl.

TABLE 1

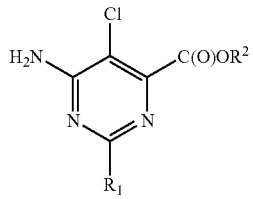

| R¹ | R² |
|---|---|
| c-Pr | CH₂CH₃ |
| c-Pr | CH₃ |
| c-Pr | H |
| c-Pr | i-Pr |
| c-Pr | CH₂CH₂CH₃ |
| c-Pr | CH₂CH₂CH₂CH₃ |
| c-Pr | i-Bu |
| c-Pr | (CH₂)₇CH₃ |
| c-Pr | CH(CH₃)(CH₂)₅CH₃ |
| c-Pr | CH₂CH(C₂H₅)(CH₂)₃CH₃ |
| 4-Cl—Ph | CH₂CH₃ |
| 4-Cl—Ph | CH₃ |
| 4-Cl—Ph | H |
| 4-Cl—Ph | i-Pr |
| 4-Cl—Ph | CH₂CH₂CH₃ |
| 4-Br—Ph | CH₂CH₃ |
| 4-Br—Ph | CH₃ |
| 4-Br—Ph | H |

TABLE 2

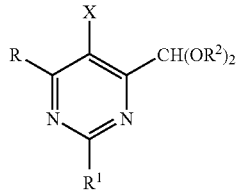

| R | X | R¹ | R² |
|---|---|---|---|
| NH₂ | Cl | c-Pr | CH₂CH₃ |
| NH₂ | Cl | c-Pr | CH₃ |
| NH₂ | Cl | c-Pr | i-Pr |
| NH₂ | Cl | c-Pr | CH₂CH₂CH₃ |
| NH₂ | Cl | c-Pr | CH₂CH₂CH₂CH₃ |
| NH₂ | Cl | c-Pr | i-Bu |
| NH₂ | Cl | c-Pr | (CH₂)₇CH₃ |
| NH₂ | Cl | c-Pr | CH(CH₃)(CH₂)₅CH₃ |
| NH₂ | Cl | c-Pr | CH₂CH(C₂H₅)(CH₂)₃CH₃ |
| NH₂ | Cl | 4-Cl—Ph | CH₂CH₃ |
| NH₂ | Cl | 4-Cl—Ph | CH₃ |
| NH₂ | Cl | 4-Cl—Ph | i-Pr |
| NH₂ | Cl | 4-Cl—Ph | CH₂CH₂CH₃ |
| NH₂ | Cl | 4-Br—Ph | CH₂CH₃ |
| NH₂ | Cl | 4-Br—Ph | CH₃ |
| Cl | Cl | c-Pr | CH₂CH₃ |
| Cl | Cl | c-Pr | CH₃ |
| Cl | Cl | c-Pr | i-Pr |
| Cl | Cl | c-Pr | CH₂CH₂CH₃ |
| Cl | Cl | c-Pr | CH₂CH₂CH₂CH₃ |
| Cl | Cl | c-Pr | i-Bu |
| Cl | Cl | c-Pr | (CH₂)₇CH₃ |
| Cl | Cl | c-Pr | CH(CH₃)(CH₂)₅CH₃ |
| Cl | Cl | c-Pr | CH₂CH(C₂H₅)(CH₂)₃CH₃ |
| Cl | Cl | 4-Cl—Ph | CH₂CH₃ |
| Cl | Cl | 4-Cl—Ph | CH₃ |
| Cl | Cl | 4-Cl—Ph | i-Pr |
| Cl | Cl | 4-Cl—Ph | CH₂CH₂CH₃ |
| Cl | Cl | 4-Br—Ph | CH₂CH₃ |
| Cl | Cl | 4-Br—Ph | CH₃ |
| OH | Cl | c-Pr | CH₂CH₃ |
| OH | Cl | c-Pr | CH₃ |

TABLE 2-continued

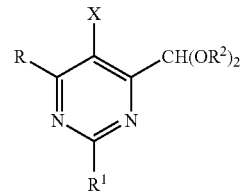

| R | X | R¹ | R² |
|---|---|---|---|
| OH | Cl | c-Pr | i-Pr |
| OH | Cl | c-Pr | CH₂CH₂CH₃ |
| OH | Cl | c-Pr | CH₂CH₂CH₂CH₃ |
| OH | Cl | c-Pr | i-Bu |
| OH | Cl | c-Pr | (CH₂)₇CH₃ |
| OH | Cl | c-Pr | CH(CH₃)(CH₂)₅CH₃ |
| OH | Cl | c-Pr | CH₂CH(C₂H₅)(CH₂)₃CH₃ |
| OH | Cl | 4-Cl—Ph | CH₂CH₃ |
| OH | Cl | 4-Cl—Ph | CH₃ |
| OH | Cl | 4-Cl—Ph | i-Pr |
| OH | Cl | 4-Cl—Ph | CH₂CH₂CH₃ |
| OH | Cl | 4-Br—Ph | CH₂CH₃ |
| OH | Cl | 4-Br—Ph | CH₃ |
| OH | H | c-Pr | CH₂CH₃ |
| OH | H | c-Pr | CH₃ |
| OH | H | c-Pr | i-Pr |
| OH | H | c-Pr | CH₂CH₂CH₃ |
| OH | H | c-Pr | CH₂CH₂CH₂CH₃ |
| OH | H | c-Pr | i-Bu |
| OH | H | c-Pr | (CH₂)₇CH₃ |
| OH | H | c-Pr | CH(CH₃)(CH₂)₅CH₃ |
| OH | H | c-Pr | CH₂CH(C₂H₅)(CH₂)₃CH₃ |
| OH | H | 4-Cl—Ph | CH₂CH₃ |
| OH | H | 4-Cl—Ph | CH₃ |
| OH | H | 4-Cl—Ph | i-Pr |
| OH | H | 4-Cl—Ph | CH₂CH₂CH₃ |
| OH | H | 4-Br—Ph | CH₂CH₃ |
| OH | H | 4-Br—Ph | CH₃ |

What is claimed is:

1. A method for preparing a compound of Formula 1,

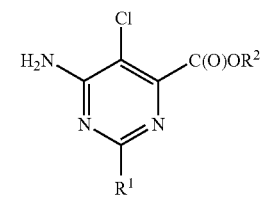

wherein $R^1$ is cyclopropyl, 4-chlorophenyl or 4-bromophenyl; and $R^2$ is $C_1$-$C_{14}$ alkyl; comprising contacting a compound of Formula 2

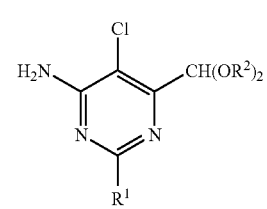

with a persulfate oxidant in the presence of a strong sulfur- or phosphorus-containing mineral acid.

2. The method of claim 1 wherein the strong sulfur-containing mineral acid is sulfuric acid.

3. The method of claim 1 further comprising preparing the compound of Formula 2 by contacting a compound of Formula 3

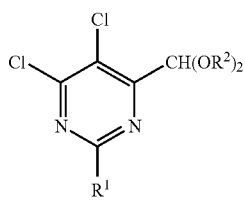
3 with ammonia.

4. The method of claim 3 further comprising preparing the compound of Formula 3 by contacting a compound of Formula 4

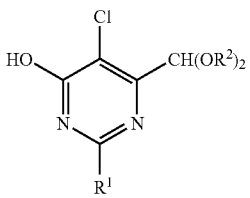
4 with a dehydroxylating-chlorinating agent selected from phosphorus oxychloride and thionyl chloride in the presence of N,N-dimethylformamide.

5. The method of claim 4 further comprising preparing the compound of Formula 4 by contacting a compound of Formula 5

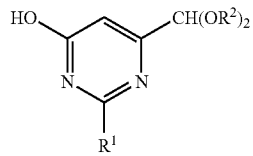
5 with a chlorinating agent.

6. A compound of Formula 6, or a salt thereof,

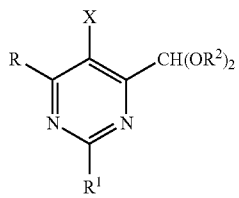
6 wherein R is $NH_2$, Cl or OH; X is Cl; $R^1$ is cyclopropyl, 4-chlorophenyl or 4-bromophenyl; and $R^2$ is $C_1$-$C_{14}$ alkyl.

7. The compound of claim 6 wherein R is $NH_2$.
8. The compound of claim 6 wherein R is Cl.
9. The compound of claim 6 wherein R is OH.
10. The compound of claim 6 wherein $R^1$ is cyclopropyl.
11. The compound of claim 6 wherein $R^1$ is 4-chlorophenyl or 4-bromophenyl.
12. The compound of claim 11 wherein $R^1$ is 4-chlorophenyl.
13. The compound of claim 12 wherein $R^1$ is 4-bromophenyl.
14. The compound of claim 6 wherein $R^2$ is $C_1$-$C_8$ alkyl.
15. The compound of claim 14 wherein $R^2$ is $C_1$-$C_3$ alkyl.
16. The compound of claim 15 wherein $R^2$ is methyl.

* * * * *

UNITED STATES PATENT AND TRADEMARK OFFICE
CERTIFICATE OF CORRECTION

| | |
|---|---|
| PATENT NO. | : 8,013,155 B2 |
| APPLICATION NO. | : 11/886653 |
| DATED | : September 6, 2011 |
| INVENTOR(S) | : Gary David Annis |

It is certified that error appears in the above-identified patent and that said Letters Patent is hereby corrected as shown below:

Column 5, line 14 "the contacting is performed in an non-acidic organic"
should be replaced with -- the contacting is performed in a non-acidic organic --

Column 6, line 25 "Embodiment E4. A method of Embodiment E3 wherein the"
should be replaced with -- Embodiment E4. A method of Embodiment E3 --

The unit "°C." should be replaced with -- °C -- in all of the following places

Column 5, lines 36 and 41

Column 8, lines 15 and 16

Column 9, lines 5, 10, 14, 15, 16, 60 and 62

Column 10, lines 48 and 62

Column 12, lines 29, 35 and 36

Column 13, line 60

Column 14, line 21

Column 18, line 37 in Claim 13 the phrase "compound of claim 12 wherein"
should be replaced with -- compound of claim 11 wherein --

Signed and Sealed this
Twenty-sixth Day of March, 2013

Teresa Stanek Rea
*Acting Director of the United States Patent and Trademark Office*